US011786708B2

(12) United States Patent  
Hall et al.

(10) Patent No.: US 11,786,708 B2  
(45) Date of Patent: Oct. 17, 2023

(54) INFLATABLE MEDICAL BALLOON WITH FLEX POINTS DUE TO INTERRUPTED FIBERS

(71) Applicant: C.R. Bard, Inc., Tempe, AZ (US)

(72) Inventors: Justin Hall, San Tan Valley, AZ (US); Michael Booze, Peoria, AZ (US)

(73) Assignee: C.R. BARD, INC., Franklin Lakes, NJ (US)

(*) Notice: Subject to any disclaimer, the term of this patent is extended or adjusted under 35 U.S.C. 154(b) by 185 days.

(21) Appl. No.: 16/652,604

(22) PCT Filed: Jul. 30, 2018

(86) PCT No.: PCT/US2018/044334  
§ 371 (c)(1),  
(2) Date: Mar. 31, 2020

(87) PCT Pub. No.: WO2020/027776  
PCT Pub. Date: Feb. 6, 2020

(65) Prior Publication Data  
US 2020/0230375 A1     Jul. 23, 2020

(51) Int. Cl.  
*A61M 25/10* (2013.01)

(52) U.S. Cl.  
CPC ...... *A61M 25/104* (2013.01); *A61M 25/1029* (2013.01); *A61M 2025/1031* (2013.01); *A61M 2025/1084* (2013.01)

(58) Field of Classification Search  
CPC ............... A61M 25/10; A61M 25/104; A61M 25/1027; A61M 25/1029;  
(Continued)

(56) References Cited

U.S. PATENT DOCUMENTS 6,234,995 B1    5/2001    Peacock, III  
6,977,103 B2 * 12/2005    Chen ...................... A61L 29/14  
                                              264/108  
(Continued)

FOREIGN PATENT DOCUMENTS

EP          2898920 A1    7/2015  
KR     20160003673 U   10/2016  
(Continued)

OTHER PUBLICATIONS

Laminate Definition & Meaning—Merriam-Webster, https://www.merriam-webster.com/dictionary/laminate, accessed Jan. 12, 2023, copyright 2023 Merriam-Webster, Incorporated (Year: 2023).*

*Primary Examiner* — Kankindi Rwego  
(74) *Attorney, Agent, or Firm* — Dickinson Wright PLLC; Andrew D. Dorisio

(57) ABSTRACT

A fiber-reinforced device, such as an inflatable medical balloon, includes a cylindrical central portion. The balloon includes first and second tapered portions connected to the cylindrical central portion along a longitudinal axis extending from a first end of the balloon to a second end of the balloon. In one embodiment, the balloon includes at least one zone free of fibers extending in a longitudinal direction, such that each longitudinal fiber is discontinuous in a circumferential direction around the balloon. In another embodiment, the balloon includes alternating discontinuous and continuous longitudinal fibers. In yet another embodiment, the balloon includes discontinuous longitudinal fibers, with every other longitudinal fiber having a discontinuity aligned in a circumferential direction. Related methods are also disclosed.

20 Claims, 5 Drawing Sheets

(58) Field of Classification Search
CPC .. A61M 2025/1031; A61M 2025/1043; A61M 2025/1075; A61M 2025/1081; A61M 2025/1084; A61M 2025/1086; A61M 29/00; A61F 2/958
USPC .......................................................... 606/194
See application file for complete search history.

(56) References Cited

U.S. PATENT DOCUMENTS

| | | |
|---|---|---|
| 2001/0043998 A1 | 11/2001 | Chen et al. |
| 2004/0068285 A1 | 4/2004 | Burgmeier et al. |
| 2004/0082965 A1* | 4/2004 | Beckham .............. B29C 65/002 606/192 |
| 2008/0033477 A1* | 2/2008 | Campbell ........... A61M 25/104 606/194 |
| 2008/0183132 A1* | 7/2008 | Davies ................ A61M 25/104 604/103.09 |
| 2009/0012610 A1 | 1/2009 | Olson et al. |
| 2009/0038752 A1* | 2/2009 | Weng ................ A61M 25/1029 604/103.09 |
| 2010/0076401 A1* | 3/2010 | Von Oepen ............. A61F 2/958 604/509 |
| 2010/0243135 A1* | 9/2010 | Pepper .................. A61M 25/10 156/189 |
| 2013/0190796 A1* | 7/2013 | Tilson ..................... A61F 2/958 606/192 |
| 2014/0243874 A1 | 8/2014 | Pepper et al. |
| 2018/0193609 A1 | 7/2018 | Lally et al. |
| 2018/0304054 A1* | 10/2018 | McCleary ......... A61M 25/1029 |

FOREIGN PATENT DOCUMENTS

| | | |
|---|---|---|
| WO | 2006029136 A1 | 3/2006 |
| WO | 2008020980 A1 | 2/2008 |
| WO | 2013184945 A1 | 12/2013 |

* cited by examiner

INFLATABLE MEDICAL BALLOON WITH FLEX POINTS DUE TO INTERRUPTED FIBERS

INCORPORATION BY REFERENCE

All publications and patent applications mentioned in this specification are herein incorporated by reference to the same extent as if each individual publication or patent application was specifically and individually indicated to be incorporated by reference.

TECHNICAL FIELD

This disclosure pertains to devices for providing endovascular treatment and, in particular, an inflatable medical balloon with flex points created by the presence of interrupted fibers.

BACKGROUND

Fiber based devices and expandable devices, such as balloons, are widely used in medical procedures. In the case of a balloon, it is inserted, typically on the end of a catheter, until the balloon reaches the area of interest. Adding pressure to the balloon causes the balloon to inflate. In one variation of use, the balloon creates a space inside the body when the balloon inflates.

Balloons may be used in the heart valves, including during Balloon Aortic Valvuloplasty (BAV) and Transcatheter Aortic Valve Implantation (TAVI). The balloons can be used to open a stenosed aortic valve. A stenosed valve may have hard calcific lesions which may tend to tear or puncture a balloon. Additionally, a precise inflated balloon diameter may be desired for increased safety and control.

Balloons may be used to move plaque away from the center of a vascular lumen toward the vasculature walls, such as during an angioplasty or a peripheral vasculature procedure. During this procedure, a balloon tipped catheter is placed in a vascular obstruction. As the balloon is inflated, the vessel constriction is dilated, resulting in improved blood flow.

Two basic types of balloons are utilized: One is a high pressure, low-compliance balloon. The other is a lower pressure, high-compliance balloon.

High-compliance medical balloons are often composed of urethane, latex, silicone, PVC, Pebax, and other elastomers. As the pressure in a high-compliant balloon is increased, the balloon dimensions expand. Once the pressure is reduced, the high-compliance medical balloon may return to its original shape, or near its original shape. High-compliance medical balloons can easily expand several times in volume between zero inflation pressure and burst.

Traditional high-compliance medical balloons can be inadequate for many reasons. High-compliance, or highly elastic medical balloons typically cannot reach high pressures because their walls have a low tensile strength and their walls thin out as the balloon expands. In some instances, high-compliance medical balloons provide insufficient force to complete a procedure. Exceeding the rated pressure of a high-compliance medical balloon creates an excessive risk of balloon failure which can lead to serious complications for the patient. Moreover, high-compliance medical balloons also have poor shape control. As a high-compliance medical balloon expands, it may assume a shape dictated mostly by the particulars of the environment inside the patient rather than the clinical goals. In some cases, this can be contrary to what the medical practitioner desires. Many medical procedures are predicated on forming a particular balloon shape reliably. Further, high-compliance medical balloons often suffer from poor puncture and tear resistance.

Low-compliance, high pressure medical balloons substantially retain their shape under comparatively high pressures. PET (polyethylene terephthalate) is the most common material for use in high pressure low-compliance balloons. PET is commonly used for high-performance angioplasty balloons. PET is stronger than other polymers, can be molded into a variety of shapes and can be made very thin (e.g., 5 μm to 50 μm (0.0002 in. to 0.002 in.)), thus giving these balloons a low profile. However, balloons made from PET walls are fragile and prone to tears. When pressed against a hard or sharp surface in the body, such as stenosis, PET balloons have poor puncture resistance. PET is very stiff so balloons made from PET may be difficult to pack or fold into a small diameter and may have poor trackability (i.e., the ability to slide and bend over a guidewire deployed through a tortuous vessel). Further, balloons made from PET, while stronger than most other balloons made from homogenous polymers, may still not be strong enough to hold pressures sufficient to complete certain medical procedures. Additionally, with a large balloon diameter (For example, 20 mm or greater), a PET balloon still has excessive compliance for procedures such as BAV and TAVI. Nylon balloons are an alternative material for low-compliance, high pressure balloons. However, these nylon balloons are typically weaker than PET balloons and so can contain less pressure. Nylon readily absorbs water, which can have an adverse effect on Nylon's material properties in some circumstances. Nylon has improved puncture resistance over PET and is more flexible than PET.

Fiber-reinforced composite balloons are another alternative low-compliance, high pressure medical balloon. Such fiber-reinforced composite balloons can advantageously sustain high pressures, provided precise shape control, and are highly resistant to tear and puncture. The manufacturing process for fiber-reinforced balloons, however, can be complicated and expensive, requiring the application of multiple different layers of fibers to achieve the desired support. Often, at least one of these layers consists of a fabric de-convolution pattern layer wrapped around a base balloon. Such forming and wrapping of the fabric pattern layer can be cumbersome, labor and equipment intensive, and time consuming. Further, depending upon the orientation of the fibers, the tear pattern of a fiber-reinforced balloon (sometimes referred to as its "rip" or "rip-stop" properties) upon bursting can result in enhanced difficulties in removing the balloon through a shaft.

Thus, there exists the need to create a fiber-reinforced device, such as a balloon, that can be manufactured quickly and easily, with a low profile and enhanced trackability, while still maintaining its ability to withstand high pressures, provide precise shape control, and have highly controlled tear properties.

SUMMARY OF THE DISCLOSURE

One object of the invention is thus to create a fiber-reinforced inflatable device, such as a medical balloon, that can be manufactured quickly and easily, with a low profile and enhanced trackability provided by the inclusion of flex points created by fiber interruptions, while still maintaining its ability to withstand high pressures, provide precise shape control, and have highly controlled tear properties.

In general, in one embodiment, this object is achieved by providing an apparatus for performing a medical procedure, comprising an inflatable balloon including a wall having a plurality of longitudinal fibers. The wall includes at least one zone surrounding the inflatable balloon in a circumferential direction that is entirely unoccupied by the plurality of longitudinal fibers.

In one embodiment, the at least one zone is located on a generally cylindrical portion of the inflatable balloon, but could be located on the tapered or conical portions instead. The inflatable balloon may include a plurality of zones surrounding the inflatable balloon in a circumferential direction that are entirely unoccupied by the plurality of longitudinal fibers. The plurality of zones may all be located on the generally cylindrical portion of the inflatable balloon.

A further aspect of the disclosure pertains to an apparatus for performing a medical procedure, comprising an inflatable balloon including a wall having a plurality of longitudinal fibers. The longitudinal fibers include a first set of at least two axially aligned first fibers creating a first discontinuity and a second set of at least two axially aligned second fibers creating a second discontinuity spaced circumferentially from the first discontinuity. At least one continuous fiber is provided adjacent to the first and second sets of fibers, such as between the axially aligned first fibers and the axially aligned second fibers.

In one embodiment, the first discontinuity is located on a generally cylindrical portion of the inflatable balloon. In this or other embodiments, the second discontinuity is located on the generally cylindrical portion of the inflatable balloon. A third fiber may create a third discontinuity axially aligned with and spaced from the first discontinuity. In one embodiment, the first and second discontinuities may be aligned in a circumferential direction. A plurality of continuous fibers may be provided adjacent to (and substantially parallel to) the first and second sets of fibers.

This disclosure also pertains to an apparatus for performing a medical procedure including an inflatable balloon having a wall having at least three longitudinal fibers juxtaposed in a circumferential direction. The at least three longitudinal fibers include a first fiber having a first discontinuity, a second fiber having a second discontinuity, and a third fiber having a third discontinuity, wherein the first and third discontinuities are aligned in the circumferential direction and the second discontinuity is offset from the first and third discontinuities in a longitudinal direction. The apparatus may further optionally include a fourth fiber juxtaposed with the third fiber, and having a fourth discontinuity aligned with the second discontinuity in the circumferential direction and offset from the first and third discontinuities in the longitudinal direction.

In some or all embodiments, the plurality of longitudinal fibers are applied over a base balloon. The plurality of longitudinal fibers may be inelastic. The balloon may further include at least one circumferential fiber, which may extend over the plurality of longitudinal fibers along the entire length of the balloon. An outer cover may also be provided for covering the inflatable balloon.

This disclosure may also be considered to apply to: (1) an apparatus for performing a medical procedure, comprising a fiber-based inflatable balloon including a zone free of longitudinal fibers extending in a circumferential direction around the balloon; (2) an apparatus for performing a medical procedure, comprising an inflatable balloon including alternating continuous and discontinuous longitudinal fibers; or (3) an apparatus for performing a medical procedure, comprising an inflatable balloon including alternating longitudinal fibers, with every other fiber having a discontinuity aligned in a circumferential direction.

Further aspects of the disclosure pertain to methods. For instance, a method of forming an inflatable balloon for performing a medical procedure includes applying a plurality of longitudinal fibers to a base balloon, and cutting each of the longitudinal fibers to form at least one circumferential zone surrounding the base balloon in which the fibers are discontinuous. The cutting step may be performed during or after the applying step.

Still further, a method of forming an inflatable balloon for performing a medical procedure, comprises alternately providing continuous and discontinuous longitudinal fibers on a base balloon. The providing step may comprise applying a continuous longitudinal fiber during a first pass, and applying a discontinuous longitudinal fiber during a second pass. Alternatively, the providing step may comprise applying a plurality of continuous longitudinal fibers to the base balloon, and cutting at least one of the longitudinal fibers.

The disclosure also pertains to a method of forming an inflatable balloon for performing a medical procedure. The method comprises alternately providing at least three discontinuous longitudinal fibers on a base balloon, with first and third longitudinal fibers each having a discontinuity aligned in a circumferential direction, and a second longitudinal fiber between the first and third longitudinal fibers having another discontinuity offset from the first discontinuities in a longitudinal direction.

In one embodiment, the providing step may comprise applying the at least three longitudinal fibers to the base balloon, each in a continuous form; and cutting the at least three continuous longitudinal fibers to form the discontinuities. In another embodiment, the providing step comprises cutting the at least three longitudinal fibers while applying the at least three longitudinal fibers to the base balloon to form the discontinuities. The method may include the step of applying a fourth fiber juxtaposed with the third fiber, and having a fourth discontinuity aligned with the second discontinuity in the circumferential direction and offset from the first and third discontinuities in the longitudinal direction.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
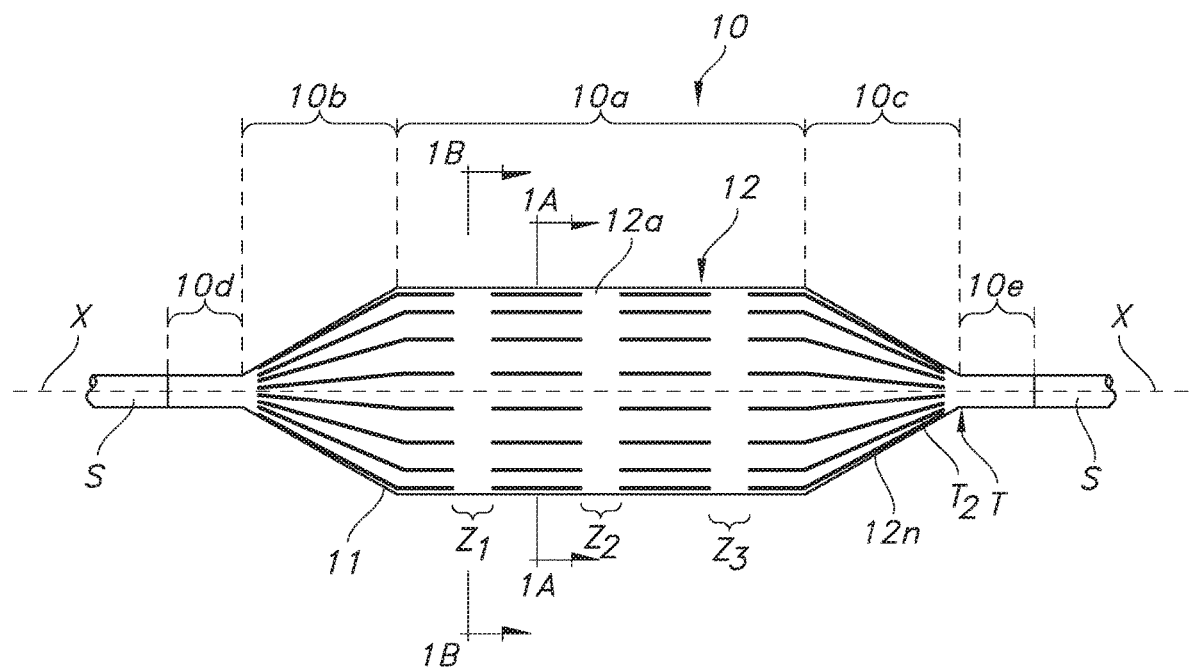
FIG. 1 shows an inflatable, fiber-based balloon that includes zones that lack longitudinally extending fibers in order to create flex points.
Figures 1A, 1B:
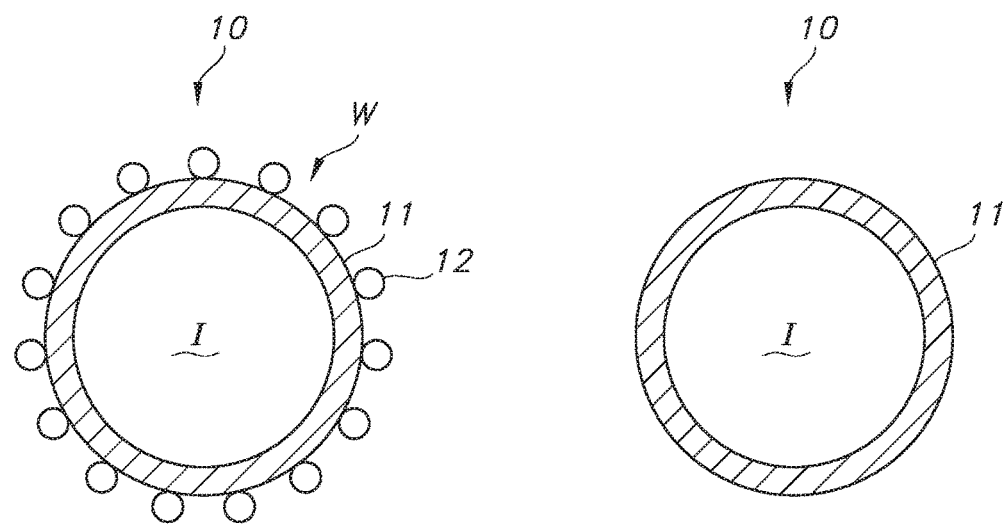
FIG. 1A is a cross-sectional view of the balloon of FIG. 1.
FIG. 1B is a cross-sectional view of the balloon of FIG. 1.

In general, and with reference to FIG. 1, described herein is a fiber-reinforced medical balloon 10, which may be a low-compliance, high pressure medical balloon, or a "non-compliant" balloon, either of which generally retains a fixed outer shape and dimension once inflated (note inner compartment I for receiving and holding inflation fluid in FIGS. 1A and 1B) and regardless of the application of additional internal pressure. The balloon 10 may be formed by the application to an outer surface of a base balloon 11 of a substantially inelastic fiber 12 to form a balloon wall W, which surrounds and forms the compartment I. The balloon 10 may include multiple passes (e.g., first, second, and third, etc.) of individual fiber strands 12a . . . 12n extending substantially parallel to the longitudinal axis X within a generally cylindrical central portion 10a (the "barrel"), from the first and second tapered portions 10b, 10c (the "cones") of the balloon 10, but stopping short of the end portions, or necks 10d, 10e (which in the illustrated embodiment extend along a shaft S, which may be sacrificial and used to support the base balloon 11 during the fiber laying process). Thus, the reduced diameter necks 10d, 10e are completely free of fiber in the illustrated embodiment, but could also serve as turnaround points for a continuously applied fiber.

According to one aspect of the disclosure, the balloon 10 may include one or more circumferentially extending zones that are entirely free of longitudinal fibers 12. As can be understood from FIGS. 1A and 1B, each zone is such that the surface of the underlying layer, such as created by a base balloon 11, is unoccupied by fibers in the zone, which completely surrounds the circumference of the balloon 10 in a linear fashion. While any number of zones may be provided, in the illustrated embodiment, three such longitudinal fiber-free zones are provided, Z1, Z2, and Z3. The zones Z1, Z2, Z3 are shown as being located on the central portion 10a, but one or more zones could instead be provided on one or both of the tapered portions 10b, 10c, or on all three portions 10a, 10b, 10c (such as one or more on each portion). The zone(s) may be of any length in the direction of the longitudinal axis, with the gap(s) or interruption (s) provided exaggerated in FIG. 1 for purposes of illustrating the concept.

In any case, it can be understood that the longitudinal fiber-free zones Z1 . . . Zn provide the balloon 10 with flex points, since the corresponding portions of the balloon do not include the layer of longitudinal fibers 12, and in the illustrated embodiment such portions are occupied only by the material of the base balloon 11 (typically, a thin layer of a flexible, polymeric material, such as nylon or PEBAX film). These flex points may allow for flexing of the balloon 10 in a direction transverse to the longitudinal axis X. Consequently, trackability of the balloon 10 through a vessel may be enhanced, as compared to the situation where the longitudinal fibers are continuously applied, or are staggered in application without creating aligned interruptions so as to form the fiber-free zones. Yet, the presence of the fibers 12 still maintains the ability of the balloon 10 to withstand high pressures, provide precise shape control, and have highly controlled tear properties.

Figure 2:
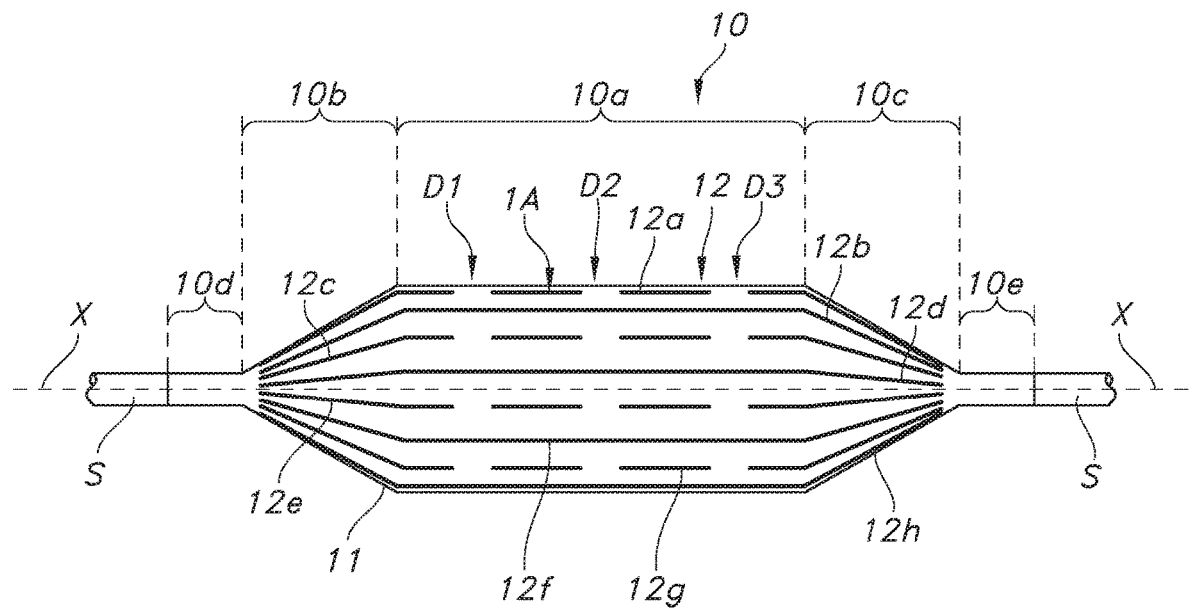
FIG. 2 shows an inflatable fiber-based balloon that includes alternating continuous and discontinuous longitudinal fibers, which also create zones of enhanced flexibility.

A further aspect of the disclosure, the longitudinal fiber strands 12a . . . 12n may be alternatively provided to the balloon 10 in a continuous and discontinuous manner. Thus, as shown in FIG. 2, a first longitudinal fiber strand 12a overlying a balloon layer (e.g., base balloon 11) is discontinuous (that is, it is comprised of a set of at least two fiber segments that are axially aligned and spaced in the longitudinal direction along the axis X to create at least one interruption), followed by a second longitudinal fiber strand 12b that is continuous. Alternating discontinuous longitudinal fiber strands 12c, 12e, 12g are provided with continuous longitudinal fiber strands 12d, 12f, 12h.

As can be understood, each discontinuous longitudinal fiber strand may have multiple interruptions (note discontinuities D1, D2, D3 in FIG. 2). Furthermore, the interruptions of the alternating discontinuous fibers may be staggered from each other along the longitudinal axis X, as shown. Alternatively, the interruptions may be aligned (not shown). In any case, the combination of alternating continuous and discontinuous fiber strands 12a . . . 12n create a balloon 10 with potentially improved trackability by enhancing transverse flexibility, while maintaining a high degree of burst strength as a result of the continuous fibers being present along the underlying balloon layer.

Figure 3:
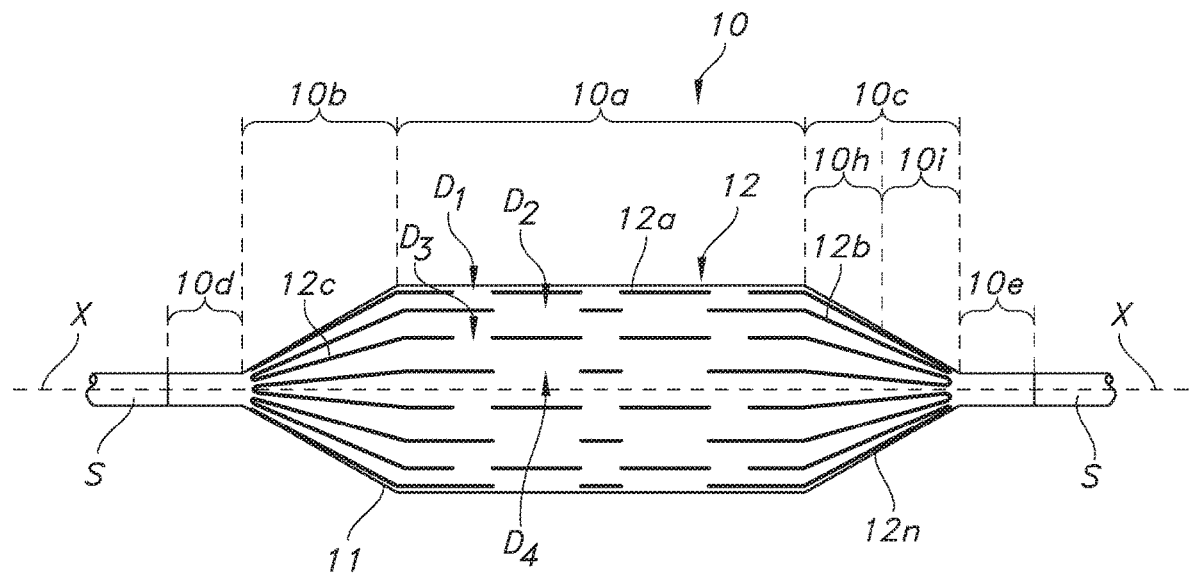
FIG. 3 shows an inflatable fiber-based balloon that includes alternating discontinuous fibers with aligned discontinuities, which also create zones of enhanced flexibility.
Figure 4:
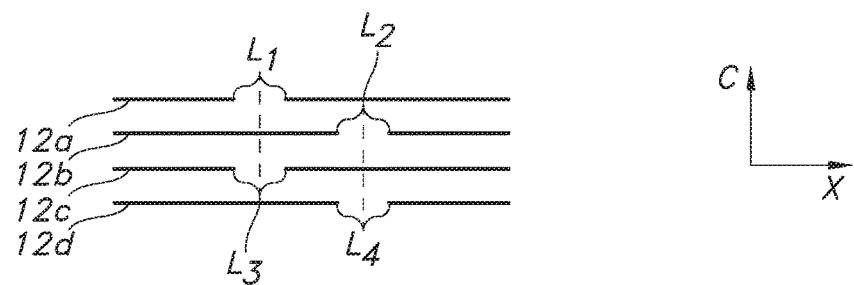
FIG. 4 is a schematic view of the alternating discontinuous fibers of the inflatable balloon of FIG. 3.

A further aspect of the disclosure is to provide aligned discontinuities on alternating longitudinal fibers 12 in juxtaposition (that is, side-by-side in the circumferential direction). Thus, as indicated in FIG. 3, a first fiber strand 12a has a first discontinuity D1, and the next-adjacent fiber strand 12b has a second discontinuity D2 that is offset or staggered along the longitudinal axis X. A third fiber strand 12c has a discontinuity D3 that is aligned with the first discontinuity D1, and a fourth fiber strand 12d has a discontinuity D4 that is offset or staggered from the first and third discontinuities, but aligned with the second discontinuity D2. This is illustrated schematically in FIG. 4, and it can be further understood that the discontinuities D1-D4 when aligned in the circumferential direction C have matching lengths (that is, the lengths L1, L3 are substantially the same in the direction of the longitudinal axis X, and the lengths L2, L4 are substantially the same in the longitudinal direction, but the lengths of the matched discontinuities L1, L3 and L2, L4 need not be the same; i.e. L1=L3; L2=L4, but L1, L3 L2, L4).

This pattern of alternating, aligned discontinuities may be repeated for all longitudinal fibers 12 surrounding the balloon 10. Further, more than one discontinuity may be provided per fiber strand 12a . . . 12n, with those additional discontinuities also aligning in the above-described manner (that is, ever other fiber strand 12a . . . 12n may have a plurality of discontinuities, with those discontinuities of every other fiber each aligning in the circumferential direction). Again, this arrangement serves to provide the balloon 10 with points of enhanced lateral flexibility for navigating or tracking through torturous anatomy, as compared to the situation where each longitudinal fiber is continuously applied without interruption.

It should be understood that only a relatively small number of fiber passes per unit of area in the circumferential direction are shown for clarity purposes. In application, the pitch can be much higher that what is shown, with the longitudinal fibers being closely spaced or perhaps even touching each other. For example, the pitch of the fiber strands 12a . . . 12n can be between 8 and 100 pitch, more narrowly, between 30 and 50 pitch, such as approximately 40 pitch. The pitch may also vary along different portions of the balloon 10.

Figure 5:
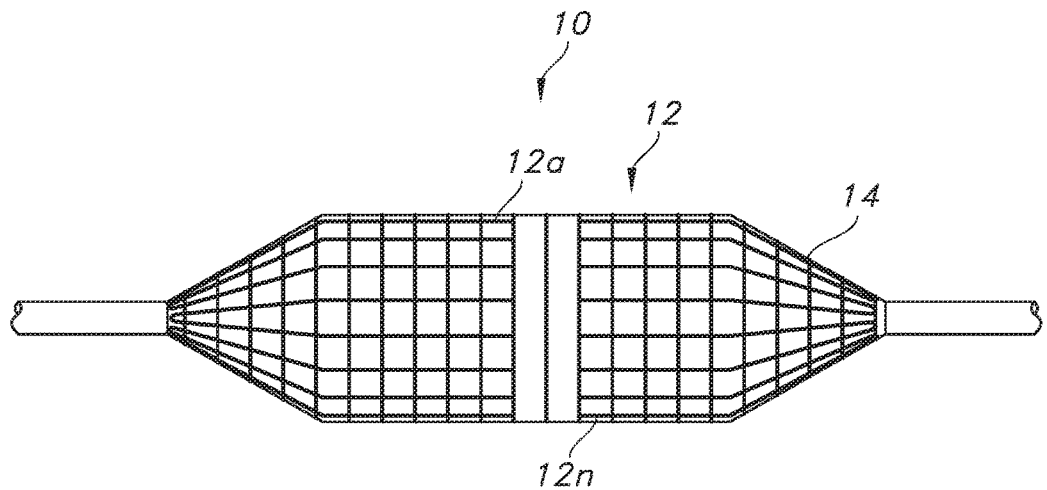
FIG. 5 illustrates the application of a circumferential or hoop fiber to the balloon.

In some embodiments, and with reference to FIG. 5, a hoop fiber 14 may be optionally provided. This hoop fiber 14 may be applied over the longitudinal fibers 12, or under it (that is, prior to the application of the longitudinal fibers). In one embodiment, the hoop fiber 14 may be applied over all of the fiber strands 12a . . . 12n. Thus, once the fiber strands 12a . . . 12n have been formed, the hoop fiber 14 can be wound radially around some or all of the various portions of the balloon 10 to form an overlaying fiber layer. The operation may be repeated as desired, with alternating layers of fiber strands 12a . . . 12n and hoop fibers being provided only all or only a portion of the balloon 10.

Figure 6:
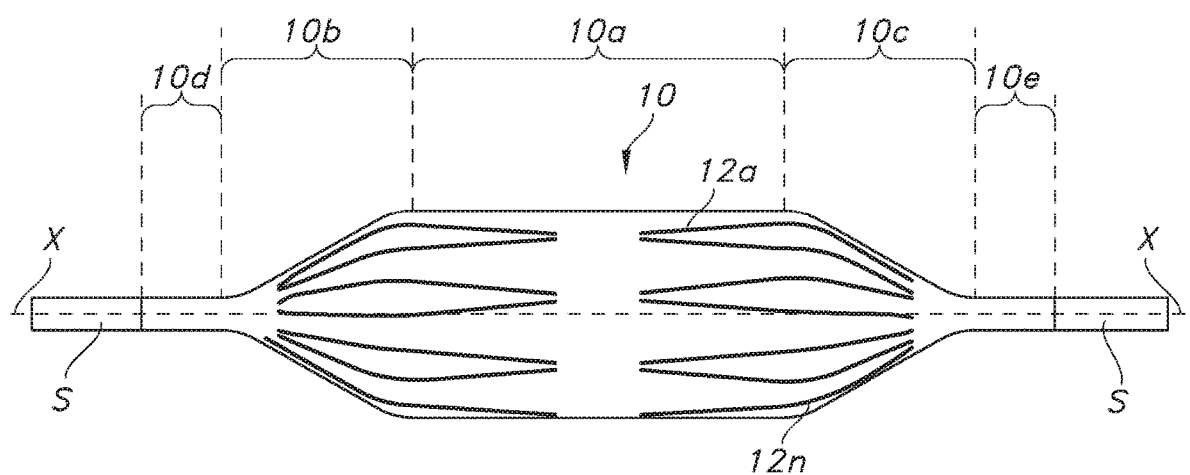
FIG. 6 illustrates the possible arrangement of the longitudinal fibers at an angle relative to the longitudinal axis of the balloon.

Referring to FIG. 6, in some embodiments, the longitudinal fiber strands 12a . . . 12n can extend at an angle relative to the longitudinal axis X within the central portion 10a. For example, the fiber strands 12a . . . 12n can extend at an angle of +/−0 to 20 degrees relative to the longitudinal axis, such as +/−5-15 degrees, such as, for instance, +/−12 degrees. Further, every other fiber strand (or alternating groups of fiber strands) can extend in opposite positive/negative directions relative to the longitudinal axis X, thereby keeping the balloon 10 from twisting. In this embodiment, the fiber strands 12a . . . 12n may optionally intersect, as illustrated, or may not (if all fiber strands have the same angular configuration and thus remain substantially parallel).

The fibers 12 described herein can be part of a fiber matrix, such as a plurality of fibers extending within a resin, adhesive, or thermally weldable material (such as a TPU). The resin, adhesive, or thermally weldable material may be applied to the fibers before, during, or after the fibers are placed on the base balloon 11 (which may be removed, if desired, once the fibers are applied).

Figure 7:
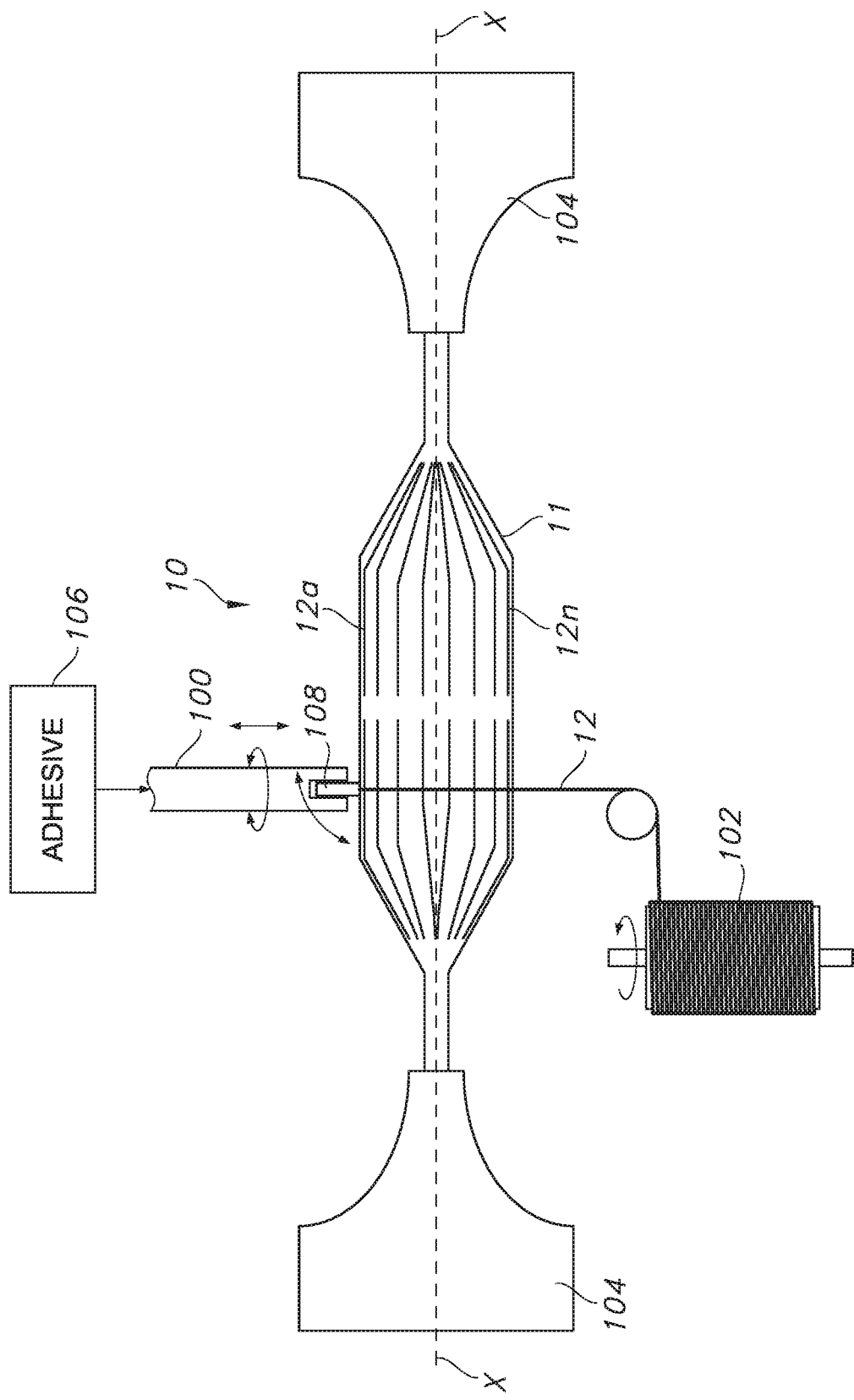
FIG. 7 illustrates one possible manner of applying a fiber to form a fiber-reinforced balloon.

Turning to FIG. 7, the longitudinal fibers 12 can be applied over the base balloon 11 using an automated applicator 100 configured to deliver the fiber from a rotatably mounted spool 102 across the surface of the balloon, which may be held in place from both ends by clamps or holders 104. Before or during the application, the longitudinal fiber(s) 12 may be infused or coated with an adhesive, a solvent, or both. The applicator 100 can rotate and translate to position the fiber 12 in contact with the base balloon 11. The applicator 100 may apply pressure normal to the surface so as to help attach the fiber 12 to the surface upon which it is being applied and/or spread monofilaments of the fiber tow.

The application of the fiber(s) 12 may involve starting at a tapered end portion 10b, 10c or necks 10d, 10e of the base balloon 11, and then extending the applicator 100 generally parallel to the longitudinal axis X. When the desired location for forming a zone free of longitudinal fiber is reached, the fiber 12 may be cut. The applicator 100 may move along the base balloon 11 a pre-determined distance (depending on the desired size of the zone) in the longitudinal direction X, and then commence the application of fiber 12 again, thus forming the desired interruption. This sequence may be repeated as desired and, as can be appreciated, may be modified in the case where the longitudinal passes are to extend at an angle relative to the longitudinal axis X. Alternatively, the longitudinal fibers 12 may be applied in a continuous fashion and then cut to form the discontinuities (alternating or continuously surrounding the circumference of the balloon 10). In either case, the cutting may be done mechanically (i.e., with a knife), with a laser, a water jet cutter, an ultrasonic blade, a heated blade or combinations thereof.

In some embodiments, an adhesive or thermally weldable material, such as thermoplastic polyurethane (TPU), can be applied to help stick the fibers 12 to the base balloon 11. The adhesive may be supplied from a reservoir 106 through a nozzle 108 adjacent the point where the fiber 12 exits the applicator 100. In the case of a hot melt glue, both the reservoir 106 and nozzle 108 may be heated to ensure that the flowability remains good.

Further, in some embodiments, the fibers 12 can be dipped through a solvated adhesive or thermally weldable material, such as TPU, during the application. In some embodiments, the material can be applied by spraying. In cases where both solvated thermally weldable material and thermally weldable material are used, the native thermally weldable material can advantageously meet the solvated thermally weldable material to help aid the adhesive properties. Adhesive or thermally weldable material can be applied during application of fiber or after the wind is concluded.

Still further, in some embodiments, an outer layer can be applied over the fiber layers. The outer layer can be formed, for example, of a panel or panels of film (not shown) wrapped around the fiber-covered balloon 10. The outer layer may also be a coating applied to the balloon 10 as a spray.

The fibers described herein can be made from a variety of materials. Exemplary materials include Vectran®, PBO, Spectra®, Conex®, Dyneema®, Technora®, Dacron®, Compet®, Polyester, Nylon, PEEK, PPS, Boron Fiber, Ceramic Fiber, Kevlar®, Inorganic Carbon or Carbon fiber, Inorganic silicon or high strength fiberglass, Organic polymer or aramid, Twaron®, Tungsten, Molybdenum, Stainless Steel, Nickel/cobalt alloys, Titanium alloys, and Nitinol alloys.

Advantageously, the fibers 12 described herein can be laid down continuously or intermittently with minimized tooling. The process can be automated and easily updated. The fiber application process can be performed quickly, particularly the application of the strands parallel to the longitudinal axis. Further, since the path of the applicator 100 may be controlled by a computer running software, the automated process allows for ease of changeability between different size and shapes of inflatable balloons. After a base balloon is loaded, the application of all the fiber can be accomplished automatically, with no need for human intervention.

Figure 8:
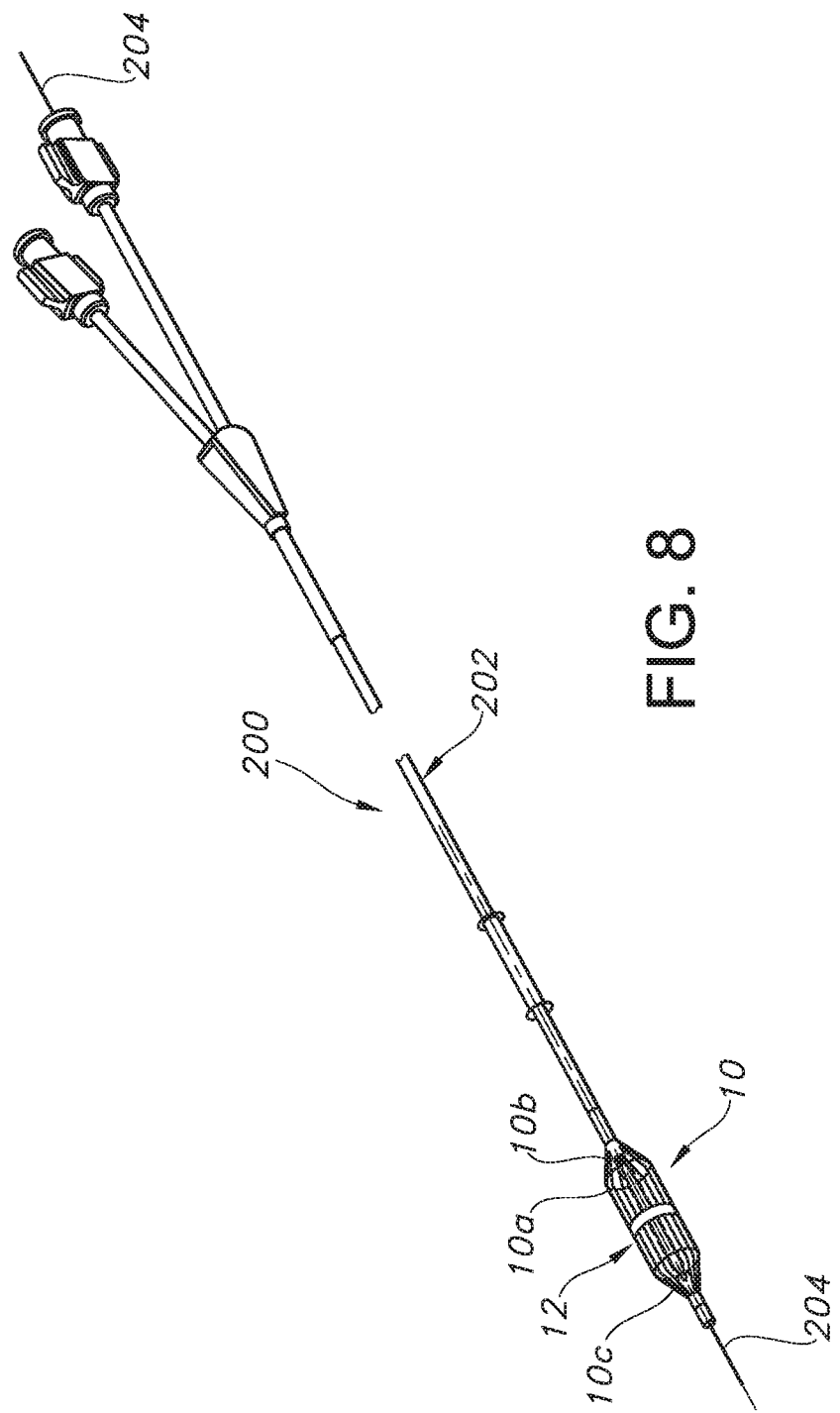
FIG. 8 is a perspective view of a catheter including a balloon formed according to the disclosed concepts.

With reference to FIG. 8, it can be understood that the fiber-based inflatable device, such as balloon 10 incorporating the fiber 12 as described above, may be provided as part of a catheter 200. The catheter 200 includes a shaft 202. The shaft 202 may have multiple lumens, such as for providing an inflation fluid to the balloon 10, and accommodating a guidewire 204.

Summarizing, this disclosure pertains to any one of the following items, considered alone or in any ordered combination:

The longitudinal fibers optionally extend in the longitudinal direction, which in particular corresponds to the longitudinal axis of the balloon. The circumferential direction optionally extends perpendicular to the longitudinal direction, and in particular along the surface of the balloon.

1. An apparatus for performing a medical procedure, comprising:
an inflatable balloon including a wall having a plurality of longitudinal fibers, the wall including at least one zone at least partially or entirely surrounding the inflatable balloon in a circumferential direction that is entirely unoccupied by the plurality of longitudinal fibers or free of the plurality of longitudinal fibers. In other words, the at least one zone is a longitudinal fiber-free zone surrounding the inflatable balloon in a circumferential direction.

2. The apparatus of item 1, wherein the at least one zone is located on a cylindrical portion of the inflatable balloon.

3. The apparatus of item 1 or item 2, wherein the inflatable balloon includes a plurality of zones surrounding the inflatable balloon in a circumferential direction that are entirely unoccupied by or free from the plurality of longitudinal fibers.

4. The apparatus of any of the foregoing items, wherein the plurality of zones are located on a cylindrical portion of the inflatable balloon.

5. An apparatus for performing a medical procedure, comprising:
an inflatable balloon including a wall having a plurality of longitudinal fibers, including a first set of at least two axially aligned first fibers creating a first discontinuity, a second set of at least two axially aligned second fibers creating a second discontinuity spaced circumferentially from the first discontinuity, and at least one continuous fiber adjacent to the first and second sets of fibers.

6. The apparatus of item 5, wherein the first discontinuity is located on a cylindrical portion of the inflatable balloon.

7. The apparatus of item 5 or item 6, wherein the second discontinuity is located on the cylindrical portion of the inflatable balloon.

8. The apparatus of any of items 5-7, further including a third fiber creating a third discontinuity axially aligned with and spaced from the first discontinuity.

9. The apparatus of any of items 5-8, wherein the first and second discontinuities are aligned in a circumferential direction.

10. The apparatus of any of items 5-9, further including a plurality of continuous fibers adjacent to the first and second sets of fibers.

11. An apparatus for performing a medical procedure, comprising:
an inflatable balloon including a wall having at least three longitudinal fibers juxtaposed in a circumferential direction, including a first fiber having as first discontinuity, a second fiber having a second discontinuity, and a third fiber having a third discontinuity, wherein the first and third discontinuities are aligned in the circumferential direction and the second discontinuity is offset from the first and third discontinuities in a longitudinal direction.

12. The apparatus of item 11, further including a fourth fiber juxtaposed with the third fiber, and having a fourth discontinuity aligned with the second discontinuity in the circumferential direction and offset from the first and third discontinuities in the longitudinal direction.

13. The apparatus of any of the foregoing items, wherein the plurality of longitudinal fibers are applied over a balloon layer, such as formed by base balloon having an interior compartment.

14. The apparatus of any of the foregoing items, wherein the plurality of longitudinal fibers are inelastic.

15. The apparatus of any of the foregoing items, further including at least one circumferential fiber.

16. The apparatus of item 15, wherein the at least one circumferential fiber overlies the plurality of longitudinal fibers.

17. The apparatus of any of the foregoing items, further including an outer cover covering the inflatable balloon.

18. An apparatus for performing a medical procedure, comprising:
a fiber-based inflatable balloon including a zone free of longitudinal fibers extending in a circumferential direction around the balloon.

The features of items 1 to 17 also specify the apparatus of item 18.

19. An apparatus for performing a medical procedure, comprising:
an inflatable balloon including alternating continuous and discontinuous longitudinal fibers. The features of items 1 to 18 also specify the apparatus of item 19.

20. An apparatus for performing a medical procedure, comprising:
an inflatable balloon including alternating longitudinal fibers, with every other fiber having a discontinuity aligned in a circumferential direction. The features of items 1 to 19 also specify the apparatus of item 20.

21. A method of forming an inflatable balloon for performing a medical procedure, comprising:
applying a plurality of longitudinal fibers to a base balloon; and
cutting each of the longitudinal fibers to form at least one circumferential zone surrounding the base balloon in which the fibers are discontinuous.

22. The method of item 21, wherein the cutting step is performed during the applying step.

23. The method of item 22, wherein the cutting step is performed after the applying step is completed.

24. A method of forming an inflatable balloon for performing a medical procedure, comprising:
alternately providing continuous and discontinuous longitudinal fibers on a base balloon. The features of items 21 to 23 also specify the apparatus of item 24.

25. The method of item 24, wherein the providing step comprises:
applying a continuous longitudinal fiber during a first pass; and applying a discontinuous longitudinal fiber during a second pass.

26. The method of item 24, wherein the providing step comprises:
applying a plurality of continuous longitudinal fibers to the base balloon; and cutting at least one of the longitudinal fibers.

27. A method of forming an inflatable balloon for performing a medical procedure, comprising:
alternately providing at least three discontinuous longitudinal fibers on a base balloon, with first and third longitudinal fibers each having a discontinuity aligned in a circumferential direction, and a second longitudinal fiber between the first and third longitudinal fibers having another discontinuity offset from the first discontinuities in a longitudinal direction.

28. The method of item 27, wherein the providing step comprises:
applying the at least three longitudinal fibers to the base balloon, each in a continuous form; and cutting the at least three continuous longitudinal fibers to form the discontinuities.

29. The method of item 27 or item 28, wherein the providing step comprises cutting the at least three longitudinal fibers while applying the at least three longitudinal fibers to the base balloon to form the discontinuities.

30. The method of any of items 27-29, further including the step of applying a fourth fiber juxtaposed with the third fiber, and having a fourth discontinuity aligned with the second discontinuity in the circumferential direction and offset from the first and third discontinuities in the longitudinal direction.

Each of the following terms written in singular grammatical form: "a", "an", and "the", as used herein, means "at least one", or "one or more". Use of the phrase One or more" herein does not alter this intended meaning of "a", "an", or "the". Accordingly, the terms "a", "an", and "the", as used herein, may also refer to, and encompass, a plurality of the stated entity or object, unless otherwise specifically defined or stated herein, or, unless the context clearly dictates otherwise. For example, the phrases: "a unit", "a device", "an assembly", "a mechanism", "a component, "an element", and "a step or procedure", as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: "includes", "including", "has", "having", "comprises", and "comprising", and, their linguistic/grammatical variants, derivatives, or/and conjugates, as used herein, means "including, but not limited to", and is to be taken as specifying the stated component(s), feature(s), characteristic(s), parameter(s), integer(s), or step (s), and does not preclude addition of one or more additional component(s), feature(s), characteristic(s), parameter(s), integer(s), step(s), or groups thereof. Each of these terms is considered equivalent in meaning to the phrase "consisting essentially of." Each of the phrases "consisting of and "consists of, as used herein, means "including and limited to". The phrase "consisting essentially of" means that the stated entity or item (system, system unit, system sub-unit device, assembly, sub-assembly, mechanism, structure, component element or, peripheral equipment utility, accessory, or material, method or process, step or procedure, sub-step or sub-procedure), which is an entirety or part of an exemplary embodiment of the disclosed invention, or/and which is used for implementing an exemplary embodiment of the disclosed invention, may include at least one additional feature or characteristic" being a system unit system sub-unit device, assembly, sub-assembly, mechanism, structure, component or element or, peripheral equipment utility, accessory, or material, step or procedure, sub-step or sub-procedure), but only if each such additional feature or characteristic" does not materially alter the basic novel and inventive characteristics or special technical features, of the claimed item.

The term "method", as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Terms of approximation, such as the terms about, substantially, approximately, etc., as used herein, refers to ±10% of the stated numerical value. Use of the terms parallel or perpendicular are meant to mean approximately meeting this condition, unless otherwise specified.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment may also be illustratively described and presented in the context or format of a plurality of separate embodiments.

Although the inventions of this disclosure have been illustratively described and presented by way of specific exemplary embodiments, and examples thereof, it is evident that many alternatives, modifications, or/and variations, thereof, will be apparent to those skilled in the art Accordingly, it is intended that all such alternatives, modifications, or/and variations, fall within the spirit of, and are encompassed by, the broad scope of the appended claims.

The invention claimed is:

1. An apparatus for performing a medical procedure, comprising:
    an inflatable balloon including a wall having an outer surface with a plurality of fibers adhesively attached to the outer surface and forming at least one zone surrounding the inflatable balloon in a circumferential direction entirely unoccupied by fibers;
    wherein the plurality of fibers comprise longitudinally extending fibers, and further including at least one circumferential fiber.

2. The apparatus of claim 1, wherein the at least one zone is located on a generally cylindrical portion of the inflatable balloon.

3. The apparatus of claim 1 wherein the at least one zone comprises two or more zones surrounding the inflatable balloon in a circumferential direction that are entirely unoccupied by fibers.

4. The apparatus of claim 1, the at least one zone comprises two or more zones located on a generally cylindrical portion of the inflatable balloon.

5. The apparatus of claim 1, wherein the plurality of fibers are infused or coated with an adhesive, a solvent, or both the adhesive and the solvent.

6. An apparatus for performing a medical procedure, comprising:
    an inflatable balloon including a wall having an outer surface with a plurality of fibers adhesively attached to the outer surface, the plurality of fibers including a first set of axially aligned first fibers creating at least two first discontinuities, a second set of axially aligned second fibers creating at least one second discontinuity, and at least one continuous fiber between the first and second sets of fibers;
    wherein the plurality of fibers comprise longitudinally extending fibers, and further including at least one circumferential fiber.

7. The apparatus of claim 6, wherein the at least two first discontinuities are located on a generally cylindrical portion of the inflatable balloon.

8. The apparatus of claim 7, wherein the at least one second discontinuity is located on the generally cylindrical portion of the inflatable balloon.

9. The apparatus of claim 8, further including a third set of axially aligned third fibers creating a third discontinuity axially aligned with and spaced from the at least one second discontinuity.

10. The apparatus of claim 6, wherein at least one of the at least two first discontinuities and the at least one second discontinuity are aligned in a circumferential direction.

11. The apparatus of claim 6, wherein the at least one continuous fiber comprises a plurality of continuous fibers.

12. The apparatus of claim 6, wherein the second set of axially aligned second fibers create at least two second discontinuities.

13. The apparatus of claim 6, wherein the at least one continuous fiber extends along a generally cylindrical portion of the inflatable balloon.

14. The apparatus of claim 6, wherein the plurality fibers are infused or coated with an adhesive, a solvent, or both the adhesive and the solvent.

15. An apparatus for performing a medical procedure, comprising:

an inflatable balloon including a wall bounding a compartment capable of containing an inflation fluid, the inflatable balloon having at least three fibers adhesively attached to an outer surface of the wall, the at least three fibers being juxtaposed in a circumferential direction, the at least three juxtaposed fibers including a first fiber having a first discontinuity, a second fiber having a second discontinuity, and a third fiber having a third discontinuity, wherein the first and third discontinuities are aligned in the circumferential direction and the second discontinuity is offset from the first and third discontinuities in a longitudinal direction, further including at least one circumferential fiber.

16. The apparatus of claim 15, further including a fourth fiber juxtaposed with the third fiber, and having a fourth discontinuity aligned with the second discontinuity in the circumferential direction and offset from the first and third discontinuities in the longitudinal direction.

17. The apparatus of claim 15, wherein the at least three fibers are applied over a base balloon including the wall with the outer surface.

18. The apparatus of claim 15, wherein the at least three fibers are inelastic.

19. The apparatus of claim 15, wherein the at least one circumferential fiber overlies the at least three juxtaposed fibers.

20. The apparatus of claim 15, wherein the at least three fibers are infused or coated with an adhesive.

* * * * *